United States Patent [19]

Toda et al.

[11] 4,372,824
[45] Feb. 8, 1983

[54] METHOD OF MANUFACTURING OXYGEN SENSOR

[75] Inventors: Nobuhiro Toda, Aichi; Masahiko Yamada, Nagoya, both of Japan

[73] Assignee: NGK Spark Plug Co., Ltd., Nagoya, Japan

[21] Appl. No.: 243,803

[22] Filed: Mar. 16, 1981

[30] Foreign Application Priority Data

Apr. 15, 1980 [JP] Japan ................................ 55-50082

[51] Int. Cl.$^3$ .......................... C25D 5/10; C25D 5/34; C25D 5/50; C25D 7/04
[52] U.S. Cl. ........................................ 204/25; 204/26; 204/37 R; 204/38 B; 204/195 S
[58] Field of Search ............... 204/25, 26, 37 R, 38 B, 204/195 S

[56] References Cited

U.S. PATENT DOCUMENTS

| | | | |
|---|---|---|---|
| 3,978,006 | 8/1976 | Topp | 204/195 S |
| 4,297,192 | 10/1981 | Shinohara | 204/195 S |
| 4,303,490 | 12/1981 | Gold | 204/195 S |

Primary Examiner—T. Tufariello
Attorney, Agent, or Firm—Fleit & Jacobson

[57] ABSTRACT

A method of manufacturing an oxygen sensor composed of oxygen ion transmissible solid electrolyte which is operative to detect an oxygen concentration in exhaust gas delivered from an internal combustion engine for the purpose of controlling a ratio of air to fuel in a mixed gas to be supplied to the combustion engine and which comprises successive steps of adhering to the outer surface of the solid electrolyte an outside electrode having a thickness of at least $0.5\mu$ by thin film techniques, heat treating the outside electrode and providing on the outside electrode a number of holes or broken holes whose diameter or width is larger than the thickness of the outside electrode, adhering to the inner surface of the solid electrolyte a porous inside electrode by thin film technique or suspension coating process, and heat treating the inside electrode at a temperature lower than the temperature at which metals constituting the inside electrode begin to be sintered.

9 Claims, 5 Drawing Figures

Very Fine Platinum Particles

Heat Treatment at 1200°C

Heat Treatment at 1300°C

Heat Treatment at 1400°C

METHOD OF MANUFACTURING OXYGEN SENSOR

BACKGROUND OF THE INVENTION

1. Field of the Invention

This invention relates to a method of manufacturing an improved oxygen senser.

2. Description of the Prior Art

Heretofore, it has been known to use an oxygen senser which is operative to detect an oxygen concentration in exhaust gas delivered from an internal combustion engine or a combustion engine for boilers for the purpose of controlling a ratio of air to fuel in a mixed gas to be supplied to the combustion engine. The oxygen senser is composed of a detection element formed of an oxygen ion transmissible metal oxide. The detection element is provided at its inner surface exposed to a reference gas (e.g. atmospheric air) and at its outer surface exposed to a detection gas (e.g. exhaust gas ) with respective electrodes each formed of a this electrically conductive film (e.g. a platinum film) deposited thereon by non-electrolytic plating, electrolytic plating, physical treatment or the like. An electromotive force induced in the detection element is taken out of the electrodes and the difference between the oxygen partial pressure of the reference gas and the oxygen partial pressure of the detection gas is detected so as to control the ratio of air to fuel.

The oxygen senser constructed as above described must satisfy the following conditions.

(1) The electrodes must not be peeled from the detection element even when the electrodes are exposed to the detection gas at a high temperature for a long time.

(2) The oxygen senser must have a sufficiently high response property and hence must have a sufficiently large three phase boundary surface and must maintain its high response property even when it is used under severe conditions.

(3) The oxygen senser must have a stable output whose value is not shifted toward the negative side. The conventional method of manufacturing the oxygen senser heretofore proposed could not satisfy the above mentioned conditions (2) and (3). An attempt has been made to make the diameter of holes or the width of broken holes produced when the electrodes are heat treated smaller than a size corresponding to the thickness of the electrodes. Inventors' experimental tests, however, demonstrated the result that the use of the hole or broken hole having such diameter or width decreases the three phase boundary surface to degrade the characteristic, particularly, response property of the oxygen senser as shown in Example 1 in the following Table 1. The cause of this decrease of the three phase boundary surface is not clear, but would be attributable to change its quality or recrystallization of constitutional metal of the electrode or to the fact that the hole or broken hole is clogged with certain ingredients in the exhaust gas.

TABLE 1

| | Film Thickness ($\mu$) | Average Diameter or Width of Hole or Broken Hole | Response Property (msec) In the Beginning | After 100 hr | After 500 hr |
| --- | --- | --- | --- | --- | --- |
| Example 1 | About 1 | 0.3 | 420 | Immeasurable | Immeasurable |
| Example 2 | About 1 | 0.7 | 130 | 200 | 370 |
| Example 3 | About 1 | 5 | 80 | 60 | 60 |

In the above Table 1, the response property shall be understood to mean time required to decrease the output from the oxygen senser from 600 mV to 300 mV.

SUMMARY OF THE INVENTION

An object of the invention, therefore, is to provide a method of manufacturing an oxygen senser which can simultaneously satisfy the above mentioned conditions (1), (2) and (3).

A feature of the invention is the provision in a method of manufacturing an oxygen senser composed of an oxygen transmissible solid electrolyte provided at its inner and outer surfaces with inside and outside electrodes, respectively, and operative to produce between said inside and outside electrodes an electromotive force corresponding to the difference between oxygen concentration at the outer surface exposed to a detection gas and oxygen concentration at the inner surface exposed to a reference gas, the improvement comprising successive steps of adhering to the outer surface of said solid electrolyte an outside electrode having a thickness of at least $0.5\mu$ by thin film techniques, heat treating said outside electrode at a temperature higher than the temperature at which metals constituting the main ingredient of said outside electrode begin to be sintered to provide on said outside electrode a number of holes or broken holes whose diameter or width is larger than the thickness of said outside diameter, adhering to the inner surface of said solid electrolyte a porous inside electrode by thin film techniques or suspension coating process, and heat treating said inside electrode at a temperature lower than the temperature at which metals consisting of said inside electrode begins to be sintered.

Further objects and features of the invention will be fully understood from the following detailed description with reference to the accompanying drawings, in which:

DETAILED DESCRIPTION OF THE PREFERRED EMBODIMENTS

Figure 1:
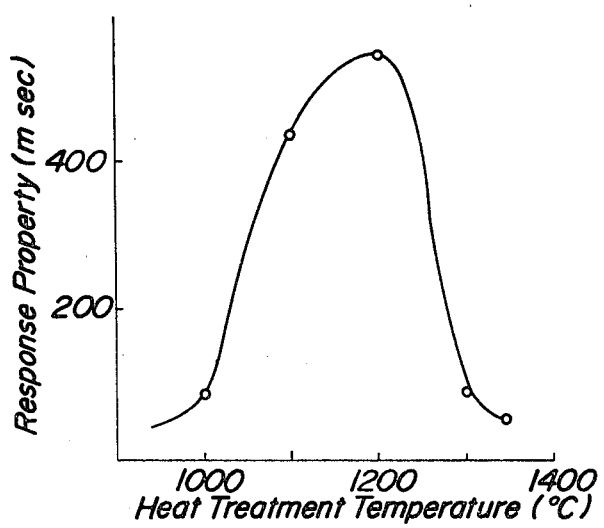
FIG. 1 is a graph illustrating the relation between the response property of an oxygen senser and a heat treatment temperature of the outside electrode.

An oxygen ion transmissible solid electrolyte, that is, a so-called oxygen concentration detection element (hereinafter will be called as a detection element) used in the method according to the invention is composed of a densely sintered body which will be produced as follows. A metal oxide such as $ZrO_2$, $ThO_2$, $CeO_2$ or the like is mixed with a metal oxide such as CaO, $Y_2O_3$, MgO or the like with a constant ratio and a mixture thus obtained is pulverized and then temporarily sintered in an electric furnace. The sintered body thus obtained is pulverized again to form a cylindrical detection element closed at its one end. The cylindrical detection element thus obtained is principally sintered at 1500° to 1800° C. to obtain the above mentioned densely sintered body. The solid electrolyte thus obtained is provided at its inner and outer side surfaces with respective electrodes, respectively. The outside electrode is exposed to a detection gas, while the inside electrode is exposed to a reference gas. The difference between the oxygen concentrations of the detection gas and reference gas is taken out of the oxygen senser as an electromotive force induced between the above mentioned two electrodes. The electrode is formed of a heat resistant metal having a catalytic action and selected from the group consisting of platinum, lutetium, rhodium, palladium, gold and silver and alloys of these metals. The electrode is usually formed of platinum or metals whose main ingredient is platinum.

The outside electrode is formed by adhering the above mentioned metals to the outer surface of the solid electrolyte by means of thin film techniques inclusive of a plating process to form a thin film having a thickness of at least 0.5μ. The outside electrode must have a thickness of at least 0.5μ in order to maintain its durability for a long time. The thin film techniques shall be understood to mean not only well known thin film techniques such as vacuum deposition, chemical deposition or the like, but also non-electrolytic plating, electric plating and a method of coating and heat decomposing metal salts on the solid electrolyte surface. Among these thin film techniques, it is preferable to use the plating method for the sake of productivity. As the plating method, use may be made of a well known non-electrolytic plating method or a combination of the non-electrolytic plating and electric plating or the like. Particularly, it is preferable to use a plating method which comprises the following three steps and which can obtain a uniformly porous and adherent and hence thick coated layer.

(a) A step of effecting the non-electrolytic plating under the condition that an active region of platinum metals is formed on the surface of the oxygen ion conductive solid electrolyte.

(b) A step of forming a relatively thin film of the platinum metals on the above mentioned active region by the non-electrolytic plating method.

(c) A step of forming a relatively thick film of platinum metals on the above mentioned relatively thin film by the electric plating method.

After the electrode metal has been coated on the outer surface of the solid electrolyte by the above mentioned method, the heat treatment is effected at a temperature that causes metals of the main ingredient of the electrode to begin to be sintered to provide on the electrode a number of holes or broken holes whose diameter or width is larger than the thickness of the electrode.

This step is led from the following experimental result. Inventors' experimental tests have demonstrated the result that if the electrode metal coated on the solid electrolyte is subjected to the heat treatment at a temperature higher than the temperature at which the electrode metal begins to be sintered, the strength of the electrode is increased as the temperature is raised, and that the porosity of the electrode is decreased as the temperature is raised, but the porosity of the electrode is again increased as the temperature is further raised.

FIG. 1 shows the relationship between the response property of the oxygen senser and the heat treatment temperature subjected to platinum metals, for example, platinum coated on the outer surface of the detection element by the plating method and having a thickness of 1μ. As can be seen from FIG. 1, if the heat treatment temperature is gradually raised from several hundreds degrees, the response property becomes gradually degraded and worse near at 1200° C. But, if the heat treatment temperature is further raised, the response property becomes improved. Experimental tests have shown the result that if the heat treatment temperature exceeds 1400° C., the resistance of the electrode becomes considerably increased. As seen from FIG. 1, if the heat treatment temperature is lower than 1000° C., the response property in the beginning is very good, but the response property of the outside electrode composed of the platinum film thus heat treated becomes suddenly deteriorated as mentioned above.

Inventors' investigations on the case of inducing the phenomenon that the response property of the oxygen sensor is changed as a function of the heat treatment temperature have demonstrated the result that the platinum subjected to the heat treatment changes its fine structure.

Figure 2A:
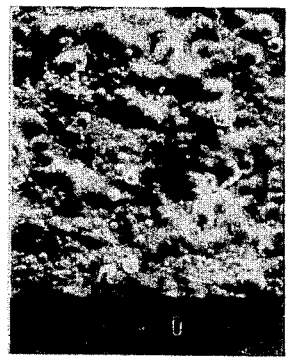
FIGS. 2A, 2B, 2C and 2D are microscope photographs.

FIGS. 2A, 2B 2C and 2D show microscope photographs of the electrode surface plated with platinum. FIG. 2A shows very fine platinum particles each having a size on the order of A and closely adhered together.

Figure 2B:
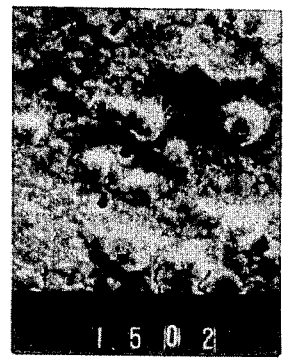
Figure 2C:
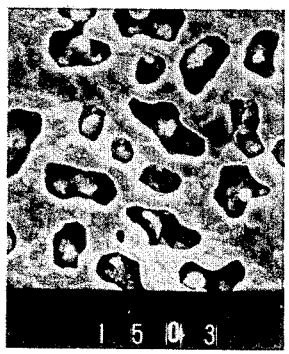
Figure 2D:
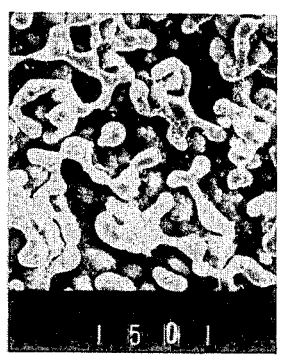

If the platinum particles are heat treated at about 1200° C., the platinum particles are sintered and become imporous as shown in FIG. 2B. If the electrode is heat treated at about 1300° C., the sintering is further advanced to produce holes or broken holes whose diameter or width is larger than the thickness of the electrode as shown in FIG. 2C. If the electrode is heat treated at about 1400° C., the sintering is excessively advanced to produce groove-shaped holes each having a width of at least 10μ and communicated with each other as shown in FIG. 2D, thereby significantly increasing the resistance of the electrode.

The above mentioned change in the fine structure of the electrode metal may be possible in the electrode thin film having a thickness within a certain limit.

Figure 3:
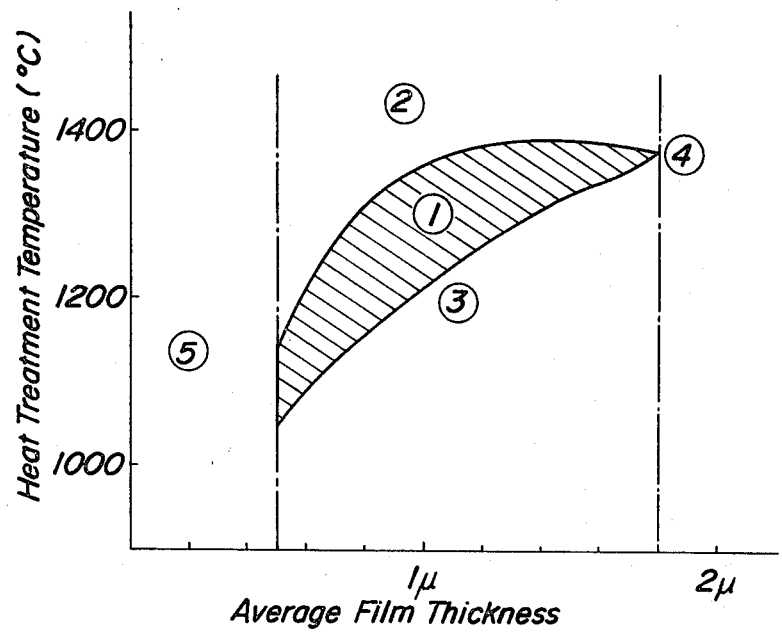
FIG. 3 is a graph illustrating the relation between the thickness of the outside electrode and the heat treatment temperature.

FIG. 3 shows the relationship between the average film thickness of the outside platinum electrode coated by the plating method and the heat treatment temperature. As can be seen from FIG. 3, the thickness of the outside electrode is limited to 0.5μ to 1.8μ. In FIG. 3, reference numeral ① designates a region in which holes or broken holes whose diameter or width is at least equal to the film thickness are produced on the outside electrode, ② a region in which groove-shaped holes communicated with each other are produced on the outside electrode to make the resistance of the outside electrode excessively high, ③ a region in which the holes or broken holes are excessively small to make the response property insufficient or make the response property deteriorate when the outside electrode is used, ④ a region in which holes or broken holes are not substantially produced on the outside electrode, but a number of minute cavities 3 (FIG. 4) are produced between the outside electrode metal film 2 and the outer surface of the solid electrolyte surface, and 5 a region in which the thickness of the electrode is excessively small and hence the holes or broken holes are excessively small, thereby making the durability of the outside electrode poor and the holes tend to be easily changed when subjected to the heat treatment into groove-shaped holes communicated with each other.

Inventors' experimental tests and investigations have demonstrated the result that the lower limit of the diameter of the hole or the width of the broken hole is preferably equal to at least the thickness of the outside electrode and that the upper limit thereof is preferably equal to at most 10 times the thickness of the outside electrode. If the diameter of the hole or the width of the broken hole exceeds 10 times the thickness of the outside electrode, communicated groove-shaped holes are produced and there is a risk of the resistance of the electrode being increased.

In the present invention, the thickness of the outside electrode is determined to $0.5\mu$ to $1.8\mu$, preferably $0.7\mu$ to $1.5\mu$ owing to the above described reasons.

The inside electrode exposed to the reference gas will now be described.

Figure 4:
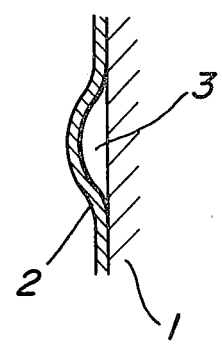
FIG. 4 is a cross-sectional view of a minute cavity formed between the electrode and the solid electrolyte surface when the electrode is heat treated.
Figure 5A:
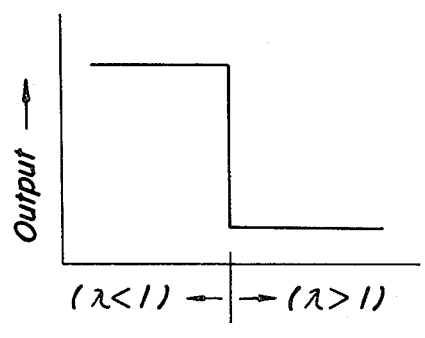
FIGS. 5A and 5B are waveform diagrams illustrating the phenomenon of shifting the oxygen senser output toward the minus side which is considered to be induced by the presence of the cavity shown in FIG. 4.
Figure 5B:
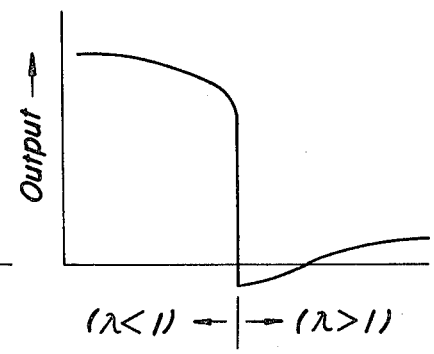

The inside electrode is not exposed to the detection gas and always lies in the oxidizing atmospheric air and hence is not required to have excellent strength and durability. It is preferable that the inside electrode must satisfy the practical requirement that the inside electrode has a large three phase boundary surface and the senser output has a normal characteristic shown in FIG. 5A rather than an abnormal characteristic in which the output becomes negative as shown in FIG. 5B. Inventors have found out that in order to satisfy such practical requirement the inside electrode must be heated at a temperature which is lower than the temperature at which the electrode metal begins to be sintered, and that the inside electrode must have a surface fine structure shown in FIG. 2A. That is, in the present invention, the inside electrode is formed by the thin film techniques inclusive of the plating method without sintering it and made porous. As the method of forming the inside electrode, use may be made of not only the above mentioned thin film techniques, but also a method of coating a suspension liquid of the electrode metal on the solid electrolyte surface. The size of the hole produced in the inside electrode is not limited with respect to the durability thereof. The inside electrode is only required to have a three phase boundary surface which is sufficiently porous. Among the methods of forming the inside electrode, it is preferable to use a plating method, particularly a method comprising successive steps of effecting non-electrolytic plating under the condition of forming an active region of the platinum metal on the solid electrolyte surface and effecting non-electrolytic plating again and effecting heat treatment at a temperature at which the electrode is not sintered for the purpose of obtaining an excellent productivity and uniform porous property. The above mentioned heat treatment is suitably effected for the purpose of improving the adhesive strength between the electrode metal and the solid electrolyte surface. The temperature at which the electrode metal is not sintered is about 900° C. for the electrode formed of platinum. If the heat treatment is effected at a temperature at which the electrode metal becomes sintered, a number of minute cavities 3 are produced between the detection element surface 1 and the electrode 2 as shown in FIG. 4. The presence of such cavities causes the output from the detection element to be shifted toward the minus side when the oxygen becomes lean as shown in FIG. 5.

The invention will now be described in detail with reference to the following embodiment.

EXAMPLE

Use was made of a tubular sintered body closed at its one end and formed of zirconia partially stabilized by yttrium oxide. The tubular sintered body was formed with an outside electrode to be exposed to the detection gas by the following steps.

Step 1: Active region forming non-electrolytic plating step.

A platinum supply liquid having a platinum concentration of 0.05 g/l was prepared by 1:1 of hexaamine platinum chloride to ammonia water. To 100 parts of the platinum supply liquid and a reducing agent was added 0.5 part of boron hydride sodium having a concentration of 100 g/l to obtain a non-electrolytic bath. Into the non-electrolytic bath was immersed the tubular sintered body formed of zirconia and the bath was heated to 65° C. and left the bath as it was for 10 minutes, thereby obtaining a tubular sintered body uniformly adhered with active region.

Step 2: Thin film forming non-electrolytic plating step.

The hexaamine platinum chloride was sampled such that the amount of platinum per one detection element was 5 mg. To this chloride was added pure water to prepare a platinum supply liquid having a platinum concentration of 0.1 g/l. To the platinum supply liquid was added 1.5 mol of 85% hydrazine hydrate with respect to 1 mol of platinum to obtain a non-electrolytic plating bath. Into this plating bath was immersed the tubular sintered body formed with the active region and the plating bath was heated to 75° C. Then, the plating bath was left as it was for 1.5 hours, thereby adhering a relatively thin platinum film having a thickness of about $0.3\mu$ to the outer surface of the tubular sintered body.

Step 3: Thick film forming electric plating step.

Use was made of platinum plating liquid available in market and having a platinum concentration of 5 g/l and a current density of 0.8 A/dm. The electric plating was effected under the above condition for 10 minutes. A relatively thick platinum film having a total thickness of about $1\mu$ was obtained.

Step 4: Heat treatment step.

The tubular sintered body was heated in an electric furnace at 1300° C. for 1 hour to obtain an outside electrode formed with a number of holes or broken holes whose average diameter or width was about $5\mu$ to $6\mu$.

Step 5: Ceramic injection step.

To the outside electrode was adhered spinel powders of magnesium aluminate having a thickness of about $100\mu$ by plasma injection.

The inside electrode to be exosed to the detection gas was formed by the following steps.

Step 6: Active region forming non-electrolytic plating step.

A platinum supply liquid having a platinum concentration of 0.05 g/l was prepared by 1:1 of hexaamine platinum chloride to ammonia water. To 100 parts of the platinum supply liquid and a reducing agent was added 0.5 part of boron hydride sodium having a concentration of 100 g/l to obtain a non-electrolytic plating liquid. This non-electrolytic plating liquid was introduced into the tubular sintered body subjected to the step 5. The tubular sintered body was heated to 80° C. and left as it was for 10 minutes to form on the tubular sintered body the uniform active region.

Step 12: Thin film non-electrolytic plating step.

The hexaamine platinum chloride was sampled such that the amount of platinum per one detective element was 5 mg. To this chloride was added pure water to prepare a platinum supply liquid having a platinum concentration of 10 g/l. To the platinum supply liquid was added 1.5 mol of 85% hydrazine hydride with respect to 1 mol of platinum to obtain a non-electrolytic plating bath. This plating bath was introduced into the tubular sintered body formed with the active region and the plating bath was heated to 85° C. Then, the plating bath was left as it was for 2.5 hours, thereby adhering a thin platinum film having a thickness of about $1\mu$ to the inner surface of the tubular sintered body.

Step 13: Heat treatment step.

The tubular sintered body was heated in an electric furnace at 650° C. for 1 hour to obtain an inside electrode formed with a number of holes or broken holes whose average diameter or width was considerably smaller than the thickness of the inside electrode.

Experimental tests have demonstrated the result that the oxygen senser manufactured by the above mentioned embodiment of the invention has a response property as shown by the example 3 in the above Table 1 and an excellent durability and shows a stable output characteristic without shifting toward the minus side even when the oxygen becomes lean.

What is claimed is:

1. In a method of manufacturing an oxygen senser having an oxygen ion transmissible solid electrolyte, an inside electrode adhered to an inner surface of said electrolyte, and an outside electrode adhered to an outside surface of said electrolyte, said senser being operative to produce between said inside and outside electrodes an electromotive force corresponding to the difference between an oxygen concentration at the outer surface exposed to a detection gas and an oxygen concentration at the inner surface exposed to a reference gas, the improvement comprising the successive steps of adhering to the outer surface of said solid electrolyte an outside electrode having a thickness of at least $0.5\mu$ by thin film techniques, heat treating said outside electrode at a temperature higher than the temperature at which a metal constituting the main ingredient of said outside electrode begins to be sintered to provide on said outside electrode a number of holes or broken holes whose diameter or width is larger than the thickness of said outside electrode, adhering to the inner surface of said solid electrolyte a porous inside electrode by thin film techniques or a suspension coating process, and heat treating said inside electrode at a temperature lower than the temperature at which a metal constituting said inside electrode begins to be sintered.

2. The method according to claim 1, wherein said outside electrode is formed of platinum or metals whose main ingredient is platinum and has a thickness of $0.5\mu$ to $1.8\mu$, said outside electrode being heat treated at 1100° C. to 1350° C.

3. The method according to claim 1, wherein said outside electrode is adhered to the outer surface of said solid electrolyte by a plating method and said inside electrode is also adhered to the inner surface of said solid electrolyte by the plating method.

4. The method according to claim 1, wherein said inside electrode is formed of platinum or metals whose main ingredient is platinum and has a thickness of about $1\mu$, said inside electrode being heat treated at 650° C.

5. The method according to claim 1, wherein each of said outside and inside electrodes is formed of heat resistant metals having a catalytic action and selected from the group consisting of platinum, lutetium, rhodium, palladium, gold, and silver and of alloys of these metals.

6. The method according to claim 1, wherein the diameter or width of said holes or broken holes on said outside electrode is at most 10 times the thickness of said outside electrode.

7. The method according to claim 1, wherein said outside electrode is formed of platinum or metals whose main ingredient is platinum and has a thickness of $0.5\mu$ to $1.8\mu$.

8. The method according to claim 7, wherein the thickness of said outside electrode is $0.7\mu$ to $1.5\mu$.

9. In an oxygen senser having an oxygen ion transmissible solid electrolyte, an inside electrode adhered to an inner surface of said electrolyte, and an outside electrode adhered to an outside surface of said electrolyte, said senser being operative to produce between said inside and said outside electrodes an electromotive force corresponding to the difference between an oxygen concentration at the outer surface exposed to a detection gas and an oxygen concentration at the inner surface exposed to a reference gas, the improvement comprising an outside electrode having a thickness of at least $0.5\mu$, said outside electrode being adhered to the outer surface of said solid electrolyte by thin film techniques and being heat treated at a temperature higher than the temperature at which a metal constituting the main ingredient of said outside electrode begins to be sintered such that said outside electrode has a number of holes or broken holes whose diameter or width is larger than the thickness of said outside electrode, and a porous inside electrode, said inside electrode being adhered to the inner surface of said solid electrolyte by thin film techniques or a suspension coating process and being heat treated at a temperature lower than the temperature at which a metal constituting said inside electrode begins to be sintered.

* * * * *